United States Patent [19]

Higo et al.

[11] Patent Number: 5,866,157
[45] Date of Patent: Feb. 2, 1999

[54] MATRIX PATCH FORMULATION

[75] Inventors: Naruhito Higo; Ken-ichi Komori; Takaaki Terahara, all of Tsukuba, Japan

[73] Assignee: Hisamitsu Pharmaceutical Co., Ltd., Saga, Japan

[21] Appl. No.: 836,975

[22] PCT Filed: Jun. 1, 1995

[86] PCT No.: PCT/JP95/01073

§ 371 Date: May 29, 1997

§ 102(e) Date: May 29, 1997

[87] PCT Pub. No.: WO96/16642

PCT Pub. Date: Jun. 6, 1996

[30] Foreign Application Priority Data

Nov. 29, 1994 [JP] Japan .................................. 6-319117

[51] Int. Cl.⁶ .................................................... A61F 13/02
[52] U.S. Cl. .......................................... 424/448; 424/449
[58] Field of Search ..................................... 424/448, 449

[56] References Cited

U.S. PATENT DOCUMENTS

| | | | |
|---|---|---|---|
| 4,322,516 | 3/1982 | Wiest | 526/307 |
| 5,225,199 | 7/1993 | Hidaka | 424/443 |
| 5,362,497 | 11/1994 | Yamada | 424/449 |
| 5,505,956 | 4/1996 | Kim | 424/448 |

*Primary Examiner*—D. Gabrielle Brouillette
*Attorney, Agent, or Firm*—Townsend & Banta

[57] ABSTRACT

A matrix type patch formulation which comprises an adhesive layer containing a physiological active substance, an organic acid, a hydrophobic high molecular material, a tackifying resin, a plasticizer and an absorption enhancer, is disclosed. The adhesive layer preferably contains 0.1 to 20% (w/w) of the physiological active substance, 0.01 to 15% (w/w) of the organic acid, 15 to 60% (w/w) of the hydrophobic high molecular material, 10 to 70% (w/w) of the tackifying resin, 10 to 60% (w/w) of the plasticizer and 0.01 to 20% (w/w) of the absorption enhancer. The organic acid is preferably an aliphatic carboxylic acid, an aromatic carboxylic acid, an alkyl sulfonic acid, an alkyl sulfonic acid derivative, cholic acid derivative or a water-soluble inorganic salt thereof. The matrix type patch formulation of the present invention can increase the percutaneous absorbability of the physiological active substance and is extremely reduced in skin irritation.

17 Claims, No Drawings

MATRIX PATCH FORMULATION

This application is a 371 of PCT/JP95/01179, filed Jun. 01, 1995.

TECHNICAL FIELD

The present invention relates to a matrix type patch formulation which increases absorbability of physiological active substances and is reduced in skin irritation.

BACKGROUND ARTS

As methods of administration of drugs, a variety of methods such as oral administration, intrarectal administration, intradermal administration, intravenous administration and the like have been known. Among them, the oral administration have been adopted widely. However, the oral administration had disadvantages i.e. that drugs are easily subject to primary metabolism in liver after absorption of the drug, and that an excess high blood concentration of drug is recognized temporally after administration. In addition, many side effects such as disturbance in gastrointestinal tracts, nausea, loss of appetite and the like have been reported in case of oral administration.

Therefore, in order to dissolve the disadvantages in association with the oral administration, the percutaneous administration method which can be expected to make absorb drugs safety and continuously, is being watched in recent years. The formulations for percutaneous administration have been developed already, and the products are on the market.

However, the percutaneous absorbability of drugs by means of the formulations for percutaneous administration are yet insufficient, and the objects are not deemed to be attained sufficiently. Namely, with the bases by itself which are used in the normal formulation for percutaneous administration, a sufficient percutaneous absorption of the formulated pharmaceutical components can not be easily attained in many cases, since normal skins have a barrier function to avoid invasions of foreign materials into body.

Thus a means to control the permeation of drugs via stratum corneum of skins and to increase the percutaneous absorbability of drugs, have been needed, and the formulation of so-called transdermal absorption enhancer in base has been attempted generally. For examples, as an absorption enhancer combining lower alkyl amide, dimethylacetamide and ethyl alcohol, isopropyl alcohol, isopropyl palmitate and the like (U.S. Pat. No. 3,472,931), an example of combination of 2-pyrrolidone and an appropriate oil, and straight-chain fatty acid and alcohol ester (U.S. Pat. No. 4,017,641), an example of lower alcohol and $C_7$–$C_{20}$ alcohol, $C_5$–$C_{30}$ aliphatic hydrocarbon, alcohol ester of $C_{19}$–$C_{26}$ aliphatic carboxylic acid, $C_{10}$–$C_{24}$ mono or dieter, $C_{11}$–$C_{15}$ ketone and water (JP A 61-249934) and the like have been proposed. However, these conventional absorption enhancers and absorption enhancing compositions can not be deemed to be sufficiently safe to skins yet.

Further, as an example of compositions of formulations for percutaneous administration, a combination of a drug and an organic acid have been reported. For examples, a tape formulation in which a combination of betamethasone valerate and an organic acid is formulated in a natural rubber pressure sensitive adhesive (JP A 56-61312), a tape formulation in which a combination of a non-steroid antiinflammatory analgesic and an organic acid is formulated in an acrylic pressure sensitive adhesive (JP A 62-126119), a pap type formulation in which a combination of methyl salicylate as a pharmaceutical component, an emulsifying agent, an organic acid, a plasticizer, a tackifying resin and water is formulated in a styrene-isoprene-styrene block copolymer (JP A 63-159315) and the like have been proposed.

However, the objects of usages of the organic acids in these examples are to improve the stability and solubility, and to control pH and the like. In addition, since these drugs are acid or neutral, these formulations are not intended to improve sufficient percutaneous permeation of the physiological substance via ion-pair formations with organic acid.

Further, there have been attempts to improve the percutaneous permeable property of basic physiological active substance. For example, a tape formulation in which a combination of citric acid and isopreterenol hydrochloride is formulated in an acrylic pressure sensitive adhesive (JP A 63-79820), a tape formulation in which a combination of an organic acid and vinpocetine is formulated in an acrylic pressure sensitive adhesive (JP A 5-25039) and the like have been reported. However, these formulations have a problems of irritation at the time of releasing, and the amount of released drug is too few to provide sufficient effects on treatment.

Thus, the present invention was made in order to dissolve the problems in relation to the prior arts, and the object of the present invention is to provide a matrix type patch formulation which increases percutaneous absorbability of the physiological active substance and is extremely reduced in irritation to skins where the formulation is applied.

DISCLOSURE OF INVENTION

The present inventors have researched earnestly in order to attain the above objects, and found that the percutaneous permeable property of drug is significantly improved and the irritation to skin where the formulation is administered is extremely reduced, by formulating a physiological active substance, an organic acid and an absorption enhancer into an adhesive layer of a matrix type patch formulation, and thus completed the present invention.

Namely, with the present invention, there is provided a matrix type patch formulation which comprises an adhesive layer containing a physiological active substance, an organic acid, a hydrophobic high molecular material, a tackifying resin, a plasticizer and an absorption enhancer.

Further, with the present invention, there is provided a matrix type patch formulation, wherein the adhesive layer contains 0.1 to 20% (w/w) of the physiological active substance, 0.01 to 15% (w/w) of the organic acid, 15 to 60% (w/w) of the hydrophobic high molecular material, 10 to 70% (w/w) of the tackifying resin, 10 to 60% (w/w) of the plasticizer and 0.01 to 20% (w/w) of the absorption enhancer.

The present invention will be explained in detail, hereinafter.

The term 'organic acid' used in the adhesive layer of the present invention implies not only organic acids and water-soluble inorganic salts thereof. As examples of the water-soluble inorganic salts, sodium salts, potassium salts, calcium salts, aluminum salts, magnesium salts and the like may be exemplified.

As examples of the organic acids and the water-soluble salts thereof, aliphatic (mono, di, tri) carboxylic acids (e.g., acetic acid, propionic acid, iso-butyric acid, caproic acid, lactic acid, maleic acid, pyruvic acid, oxalic acid, succinic acid, tartaric acid and the like), aromatic carboxylic acids (e.g., phthalic acid, salicylic acid, benzoic acid, acetyl salicylic acid and the like), alkyl sulfonic acids (e.g., ethane sulfonic acid, propyl sulfonic acid, butane sulfonic acid, polyoxyethylene alkyl ether sulfonic acid and the like), alkyl sulfonic acid derivatives (e.g., N-2-hydroxyethyl piperidine-N'-2-ethane sulfonic acid (it is abbreviated as 'HEPES' hereinafter), cholic acid derivatives (e.g., dehydrocholic acid and the like) and water-soluble inorganic acids thereof may be exemplified.

Among them, HEPES, dehydrocholic acid, sodium acetate, sodium propionate and sodium salicylate are preferable, and sodium acetate, sodium propionate and sodium salicylate are most preferable.

These organic acids may preferably be formulated in an amount from 0.01 to 15% (w/w), more preferably in an amount from 0.1 to 10% (w/w), most preferably in an amount from 0.1 to 5% (w/w), based on the total amount of the composition of the adhesive layer. If the amount of the organic acids is less than 0.01% (w/w), a sufficient permeation amount can not be obtained as a matrix type patch formulation, and if the amount exceeds 15% (w/w), the skin irritation is increased and thus it is not preferable.

In addition, as the physiological active substance formulated in the adhesive layer of the matrix type patch formulation of the present invention, any basic drug which forms ion-pair with the organic acid may be used. For examples, hypnotic-sedative agents (e.g., barbital, nitrazepam), antipyretic analgesic agents (e.g., butorphanol tartrate, pentazocine), analeptic-antihyprotic agents (e.g., methamphetamine, bemegride), anxiolytic agents (e.g., meprobamate, imipramine), local anesthetic agents (e.g., lidocaine, procaine), agents for hyperuricemia (e.g., allopurinol), agents for disturbance in micturition (e.g., oxybutynin hydrochloride), skeletal muscle relaxants (e.g., tizanidine hydrochloride, eperisone hydrochloride, pridinol mesilate), autonomic agents (e.g., carpronium hydrochloride, neostigmine oxalate), agents for Parkinson's disease (e.g., trihexyphenidyl hydrochloride, amantadine hydrochloride), antihistaminic agents (e.g., mequitazine, diphenhydramine), bronchodilator agents (e.g., tulobuterol hydrochloride, procaterol), cardiotonic agents (e.g., isoprenaline hydrochloride, aminophylline), vasodilators for coronary (e.g., diltiazem, nicorandil, nifedipine), vasodilators for blood capillary (e.g., nicametate, tolazoline hydrochloride), cardiovascular agents (e.g., flunarizine, ibudilast), antiarrhythmic agents (e.g., atenolol, alprenolol hydrochloride), antiallergic agents (e.g., ketotifen fumarate, mequitazine), antiemetic agents (e.g., betahistine, difenidol), narcotic analgesic agents (e.g., morphine, fentanyl citrate), and pharmaceutical acceptable inorganic or inorganic salts thereof may be exemplified. Among them, the bronchodilator agents, antiarrhythmic agents, narcotic analgesic agents, cardiovascular agents, skeletal muscle relaxants, and antiallergic agents are preferable.

These physiological active substances may be used alone, or two or more of them may be used together. The physiological active substances may be formulated in an amount from 0.1 to 20% (w/w) based on the total amount of the composition of the adhesive layer. If the amount is less than 0.1% (w/w), a sufficient permeation amount can not be obtained as a matrix type patch formulation, and if the amount exceeds 20% (w/w), the skin irritations such as rubor are observed, and thus it is not preferable.

As the hydrophobic high molecular material formulated in the adhesive layer of the matrix type patch formulation of the present invention, styrene-isoprene-styrene block copolymer (it is abbreviated as 'SIS' hereinafter), isoprene rubber, polyisobutylene (it is abbreviated as 'PIB' hereinafter), styrene-butadiene-styrene block copolymer (it is abbreviated as 'SBS' hereinafter), styrene-butadiene rubber (it is abbreviated as 'SBR') and acrylic polymer (copolymer of at least two materials selected from the group comprising 2-ethylhexyl acrylate, vinyl acetate, methacrylate, methoxyethyl acrylate and acrylic acid) may be exemplified. Among them, SIS, PIB and blends of the two materials are most preferable.

The hydrophobic high molecular materials may preferably be formulated in an amount from 15 to 60% (w/w), more preferably from 15 to 50% (w/w), most preferably from 20 to 40% (w/w), based on the total amount of the composition of the adhesive layer. If the amount of the hydrophobic high molecular materials is less than 15% (w/w), an adhesive layer can not be formed, and if the amount exceeds 60% (w/w), an sufficient permeable property can not be obtained and thus it is not preferable.

As the tackifying resin formulated in the adhesive layer of the matrix type patch formulation of the present invention, rosin derivatives (e.g., rosin, glycerin esters of rosin, hardened rosin, glycerin esters of hardened rosin, pentaerythritol esters of rosin and the like), alicyclic saturated hydrocarbon resins, terpene phenol, maleic acid resins and the like may be exemplified. Among them, glycerin esters of hardened rosin and alicyclic saturated hydrocarbon resins are most preferable.

The tackifying resin may preferably formulated in an amount from 10 to 70% (w/w), more preferably from 10 to 60% (w/w), most preferably from 20 to 50% (w/w), based on the total amount of the composition of the adhesive layer. If the amount of the tackifying resin is less than 10% (w/w), a sufficient adhesive force as patch formulation can not be obtained, and if the amount exceeds 70% (w/w), the adhesive force is too much increased, and skin irritation when released is increased and it is not preferable.

As the plasticizer formulated in the adhesive layer of the matrix formulation of the present invention, petroleum oils (e.g., paraffinic process oils, naphthenic process oils, aromatic process oils and the like), squalane, squalene, vegetable oils (e.g., olive oil, Tsubaki oil, castor oil, tall oil, peanut oil), dibasic acid ester (e.g., dibutyl phthalate, dioctyl phthalate and the like), liquid rubber (e.g., polybutene, liquid isoprene rubber), diethylene glycol, polyethylene glycol, glycol salicylate, propylene glycol, dipropylene glycol, crotamiton and the like may be exemplified. Among them, liquid paraffin, crotamiton, glycol salicylate, liquid polybutene and any combination of the materials are most preferable.

The plasticizer may preferably be formulated in an amount from 10 to 60% (w/w), more preferably from 15 to 50% (w/w), and most preferably from 20 to 40% (w/w), based on the total amount of the composition of the adhesive layer. If the amount of the plasticizer is less than 10% (w/w), a sufficient permeable property can not be obtained, and if the amount exceeds 60% (w/w), a sufficient cohesive force can not be kept as a patch formulation and thus it is not preferable.

As the absorption enhancer formulated in the adhesive layer of the matrix type patch formulation of the present invention, any conventional compounds whose absorption enhancing effect on skins are recognized may be used. For examples, $C_6$–$C_{20}$ fatty acids, fatty alcohols, fatty acid esters or ethers, aromatic organic acids, aromatic alcohols, aromatic organic acid esters or ethers may be exemplified, and these compounds may be saturated or unsaturated, and cyclic, straight or branched. Further, lactic acid esters, acetic acid esters, monoterpene compounds, sesquiterpene compounds, Azone, Azone derivatives, glycerin fatty acid esters, sorbitan fatty acid esters (Spans), polysorbates (Tweens), polyethylene glycol fatty acid esters, polyoxyethylene hardened castor oils (HCOs), sucrose fatty acid esters and the like may be exemplified. Concretely, caprylic acid, capric acid, lauric acid, myristic acid, palmitic acid, stearic acid, oleic acid, linolic acid, linolenic acid, lauryl alcohol, myristyl alcohol, oleyl alcohol, cetyl alcohol, methyl laurate, isopropyl myristate, myristyl myristate, octyldodecyl myristate, cetyl palmitate, methyl salicylate, cinnamic acid, methyl cinnamate, cresol, cetyl lactate, ethyl acetate, propyl acetate, geraniol, thymol, eugenol, terpineol, 1-menthol, borneol, d-limonene, isoeugenol, isoborneol, nerol, dl-camphor, glycerol monolaurate, glycerol monooleate, sorbitan monolaurate, sucrose monolaurate, polysorbate 20, polyethylene glycol monolaurate, polyethylene glycol monostearate, HCO-60 (hardened castor oil), 1-[2-(decyl thio)ethyl]azacyclopentane-2-one (it is abbreviated as 'pirotiodecane' hereinafter) are preferable, and 1-menthol, lauryl alcohol and pirotiodecane are most preferable.

The absorption enhancers may preferably be formulated in an amount from 0.01 to 20% (w/w), more preferably from 0.1 to 10% (w/w), most preferably from 0.1 to 5% (w/w), based on the total amount of the composition of the adhesive layer. If the amount of the absorption enhancer is less than 0.01% (w/w), a sufficient permeable property can not obtained as a matrix type patch formulation, and if the amount exceeds 20% (w/w), skin irritations such as rubor and edema and the like are recognized and thus it is not preferable.

In the adhesive layer of the matrix type patch formulation of the present invention, an antioxidant, fillers, a cross-linking agent, a preservative, an ultraviolet-absorber and the like may be further formulated if desired.

As the antioxidant, tocopherol and its derivatives, ascorbic acid, stearic acid esters, nor-dihydroguaiaretic acid, dibutyl hydroxytoluene (it is abbreviated as 'BHT' hereinafter), butyl hydroxy anisole and the like are preferable. The antioxidants may preferably be formulated in an amount 10% (w/w) or less, more preferably in an amount 5% (w/w) or less, and most preferably in an amount 2% (w/w) or less, based on the total amount of the composition of the adhesive layer of the matrix type patch formulation.

As the fillers, calcium carbonate, magnesium carbonate, silicates (e.g., aluminum silicate, magnesium silicate and the like), silicic acid, barium sulfate, calcium sulfate, calcium zincate, zinc oxide, titanic oxide and the like are preferable.

As the cross-linking agent, thermosetting resins such as amino resins, phenol resins, epoxy resins, alkyd resins, unsaturated polyesters, isocyanate compounds, block isocyanate compounds, organic cross-linking agents, inorganic cross-linking agents such as metal or metal compound are preferable.

As the preservative, ethyl p-oxy benzoate, propyl p-oxy benzoate, butyl p-oxy benzoate and the like are preferable.

As the ultraviolet-absorber, p-amino benzoic acid derivatives, anthranilic acid derivatives, salicylic acid derivatives, coumarin derivatives, amino acid compounds, imidazoline derivatives, pyrimidine derivatives, dioxane derivatives and the like are preferable.

The antioxidants, fillers, cross-linking agents, preservatives and ultraviolet-absorbers may preferably be formulated in an amount 10% (w/w) or less, more preferably in an amount 5% (w/w) or less, most preferably in an amount 2% (w/w) or less in all, based on the total amount of the composition of the adhesive layer.

The adhesive layer having the above composition may be prepared by any method. For example, after dissolving the base components containing drugs in an solvent such as toluene, hexane, ethyl acetate and the like, applying it onto a releasable liner paper or backing, and removing the solvent by drying, it is putted with a backing so as to have a formulation of the present invention. Further, after hot-melting the base composition containing drugs and applying it onto a backing or a releasable liner paper, the adhesive layer is putted with a backing so as to have a formulation of the present invention.

In addition, the matrix type patch formulation of the present invention may comprise a backing layer and an adhesive layer formed on it, and any other structures and materials forming each element are not limited, provided that the adhesive layer has the above composition containing the organic acid and physiological active substance. For Example, the matrix type patch formulation of the present invention may further have a releasable liner paper layer on the adhesive layer formed on the backing layer.

The backing layer may preferably comprise a soft material, for example, fabric, polyurethane, polyester, polyvinyl acetate, polyvinylidene chloride, polyethylene, polyethylene terephthalate, polybutylene terephthalate, paper, aluminum sheet and the like, or composite materials thereof.

With the matrix type patch formulation of the present invention, the physiological active substance can be absorbed via skins continuously into the circulating blood. Further, the matrix type patch formulation of the present invention is extremely reduced in skin irritation. In addition, the side-effects in digestive system which are shown when oral-administered and the side-effects in central nervous system which may be occurred accompanied with the rapid increase of blood concentration, may be inhibited.

EXAMPLES

The present invention will be explained in more detail with Examples and Comparative Examples hereinafter. However, the present invention is not limited to the Examples, and the present invention extends to all such modifications and variations as will be apparent to those skilled in the art without departing the scope of the present invention. In Examples and Comparative Examples, all '%' is % (w/w).

Example 1

| | |
|---|---:|
| SIS (Califlex D-1111; manufactured by Shell Co.) | 16.5% |
| PIB (Vistanex MM-L-100; manufactured by Exxon Co.) | 1.5% |
| PIB (Vistanex LMMH; manufactured by Exxon Co.) | 6% |
| Alicyclic saturated hydrocarbon resin (Arcon P-100; manufactured by Arakawa Kagaku Co., Ltd.) | 29.5% |
| Liquid paraffin (Crystol 352; manufactured by Esso Co.) | 39.5% |
| Pirotiodecane | 2% |
| Sodium acetate | 1.5% |
| Ketotifen fumarate | 2% |
| Aluminum silicate | 1% |
| BHT (Yoshinox BHT; manufactured by Yoshitomi Pharmaceutical Industries, Ltd.) | 0.5% |
| Total Amount | 100% |

All the components were hot-melted and applied onto a releasable liner paper to have a thickness of 100 μm, and putted together with a backing made of polyester (it was also used in Examples 2 to 17, and Comparative Examples 1 to 13) so as to obtain a matrix type patch formulation of the present invention.

Example 2

| | |
|---|---|
| SIS (Califlex D-1111) | 16.5% |
| PIB (Vistanex MM-L-100) | 1.5% |
| PIB (Vistanex LMMH) | 6% |
| Alicyclic saturated hydrocarbon resin (Arcon P-100) | 30% |
| Liquid paraffin (Crystol 352) | 37% |
| Pirotiodecane | 3% |
| Sodium acetate | 1.5% |
| Fentanyl citrate | 3% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 3

| | |
|---|---|
| SIS (Califlex D-1111) | 17.5% |
| PIB (Vistanex MM-L-100) | 2.5% |
| PIB (Vistanex LMMH) | 6% |
| Hardened rosin ester (Foral 85; manufactured by Rika Hercules Co., Ltd.) | 35% |
| Liquid paraffin (Crystol 352) | 27.6% |
| Crotamiton | 5% |
| Pirotiodecane | 3% |
| Sodium acetate | 0.4% |
| Tizanidine hydrochloride | 1.5% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 4

| | |
|---|---|
| SIS (Califlex D-1111) | 17.5% |
| PIB (Vistanex MM-L-100) | 2.5% |
| PIB (Vistanex LMMH) | 6% |
| Hardened rosin ester (KE-100; manufactured by Arakawa Kagaku Co., Ltd.) | 35% |
| Liquid paraffin (Crystol 352) | 19.5% |
| Glycol salicylate | 10% |
| l-menthol | 5% |
| Sodium salicylate | 1% |
| Tizanidine hydrochloride | 2% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 5

| | |
|---|---|
| PIB (Vistanex MM-L-100) | 38.4% |
| Hardened rosin ester (KE-311; manufactured by Arakawa Kagaku Co., Ltd. | 20% |
| Liquid paraffin (Crystol 352) | 35% |
| Liquid polybutene (HV-300; manufactured by Nippon Petrochemicals Co., Ltd.) | 5% |
| l-menthol | 0.1% |
| Sodium acetate | 0.5% |
| Tulobuterol hydrochloride | 1% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 6

| | |
|---|---|
| SIS (Califlex D-1111) | 20% |
| Hardened rosin ester (KE-311) | 50% |
| Liquid paraffin (Crystol 352) | 20% |
| Lauryl alcohol | 1% |
| Sodium propionate | 5% |
| Alprenolol hydrochloride | 3% |
| BHT (Yoshinox) | 1% |
| Total Amount | 100% |

All the components were hot-melted and applied onto a releasable liner paper to have a thickness of 100 μm, and putted together with a backing so as to obtain a matrix type patch formulation of the present invention.

Example 7

| | |
|---|---|
| SIS (Califlex D-1111) | 36.5% |
| PIB (Vistanex MM-L-100) | 3.5% |
| PIB (Vistanex LMMH) | 20% |
| Alicyclic saturated hydrocarbon resin (Arcon P-100) | 10% |
| Liquid paraffin (Crystol 352) | 15% |
| Pirotiodecane | 10% |
| Sodium propionate | 0.2% |
| Ketotifen fumarate | 3.5% |
| Aluminum silicate | 0.8% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 8

| | |
|---|---|
| PIB (Vistanex MM-L-100) | 15% |
| Hardened rosin ester (Foral 85) | 70% |
| Crotamiton | 10% |
| Pirotiodecane | 2.5% |

-continued

| | |
|---|---|
| Sodium acetate | 0.5% |
| Tizanidine hydrochloride | 2% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 9

| | |
|---|---|
| SIS(Califlex D-1111) | 10% |
| PIB(Vistanex MM-L-100) | 5% |
| Alicyclic saturated hydrocarbon resin (Arcon P-100) | 20% |
| Liquid paraffin(Crystol 352) | 18% |
| Crotamiton | 5% |
| l-menthol | 20% |
| Sodium salicylate | 15% |
| Fentanyl citrate | 5% |
| Aluminum silicate | 1% |
| BHT(Yoshinox) | 1% |
| Total Amount | 100% |

All the components were hot-melted and applied onto a releasable liner paper to have a thickness of 100 μm, and putted together with a backing so as to obtain a matrix type patch formulation of the present invention.

Example 10

| | |
|---|---|
| PIB(Vistanex MM-L-100) | 15% |
| Hardened rosin ester (Foral 85) | 10% |
| Liquid paraffin(Crystol 352) | 60% |
| Pirotiodecane | 2% |
| Sodium acetate | 10% |
| Tulobuterol hydrochloride | 3% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 11

| | |
|---|---|
| SIS(Califlex D-1111) | 26.5% |
| PIB(Vistanex MM-L-100) | 3.5% |
| PIB(Vistanex LMMH) | 20% |
| Hardened rosin ester(Foral 85) | 20% |
| Liquid paraffin(Crystol 352) | 15% |
| Lauryl alcohol | 10% |
| Sodium propionate | 0.2% |
| Alprenolol hydrochloride | 3.5% |
| Aluminum silicate | 0.8% |
| BHT(Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 12

| | |
|---|---|
| PIB(Vistanex MM-L-100) | 16% |
| Hardened rosin ester (Foral 85) | 60% |
| Crotamiton | 15% |
| Pirotiodecane | 5% |
| Sodium acetate | 1% |
| Tizanidine hydrochloride | 3% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 13

| | |
|---|---|
| SIS(Califlex D-1111) | 13.5% |
| PIB(Vistanex MM-L-100) | 4% |
| Hardened rosin ester (Foral 85) | 20% |
| Liquid paraffin (Crystol 352) | 20% |
| Liquid polybutene (HV-300) | 25% |
| Crotamiton | 5% |
| l-menthol | 5% |
| Sodium propionate | 1.2% |
| Tulobuterol hydrochloride | 5% |
| Aluminum silicate | 0.8% |
| BGH (Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 14

| | |
|---|---|
| SIS(Califlex D-1111) | 17.5% |
| PIB(Vistanex MM-L-100) | 2.5% |
| PIB(Vistanex LMMH) | 6% |
| Hardened rosin ester(Foral 85) | 35% |
| Liquid paraffin(Crystol 352) | 27.6% |
| Crotamiton | 5% |
| Pirotiodecane | 3% |
| Sodium acetate | 0.4% |
| Tulobuterol hydrochloride | 1.5% |
| Aluminum silicate | 1% |
| BHT(Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 15

| | |
|---|---|
| SIS(Califlex D-1111) | 17.5% |
| PIB(Vistanex MM-L-100) | 2.5% |
| PIB(Vistanex LMMH) | 6% |
| Hardened rosin ester (KE-100) | 35% |
| Liquid paraffin(Crystol 352) | 19.5% |
| Glycol salicylate | 10% |

-continued

| | |
|---|---|
| l-menthol | 5% |
| Sodium salicylate | 1% |
| Ketotifen hydrochloride | 2% |
| Aluminum silicate | 1% |
| BHT(Yoshinox) | 0.5% |
| Total Amount | 100% |

All the components were hot-melted and applied onto a releasable liner paper to have a thickness of 100 μm, and putted together with a backing so as to obtain a matrix type patch formulation of the present invention.

Example 16

| | |
|---|---|
| PIB(Vistanex MM-L-100) | 15% |
| Hardened rosin ester (Foral 85) | 70% |
| Crotamiton | 10% |
| Pirotiodecane | 2.5% |
| Sodium acetate | 0.5% |
| Fentanyl citrate | 2% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 17

| | |
|---|---|
| PIB (Vistanex MM-L-100) | 16% |
| Hardened rosin ester (Foral 85) | 60% |
| Crotamiton | 15% |
| Pirotiodecane | 5% |
| Sodium acetate | 1% |
| Alprenolol hydrochloride | 3% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation of the present invention.

Example 18

| | |
|---|---|
| Sodium acetate | 1.5% |
| Pirotiodecane | 2.0% |
| Liquid paraffin (Crystol 352) | 36.5% |
| Polyterpene resin tackifier | 29.5% |
| PIB (Vistanex MM-L-100) | 7.5% |
| SIS (Califlex D-1111) | 16.5% |
| BHT (Yoshinox) | 1.5% |
| Ketotifen fumarate | 5.0% |
| Total Amount | 100% |

The above components except sodium acetate, pirotiodecane and ketotifen fumarate were dissolved at 180° C. and mixed. Then the rest components were added and dispersed so as to have a homogeneous mixture. The mixture was laminated onto a PET film of 30 μm to have an adhesive layer of 100 μm, and a matrix type patch formulation of the present invention was prepared.

Example 19

| | |
|---|---|
| Sodium acetate | 5.0% |
| Liquid paraffin (Crystol 352) | 6.5% |
| Oil-soluble phenol resin tackifier (Tamanol 521; manufactured by Arakawa Kagaku Co., Ltd.) | 37.5% |
| PIB (Vistanex MM-L-100) | 7.5% |
| SIS (Califlex D-1111) | 30.5% |
| BHT (Yoshinox) | 1.0% |
| Lauryl alcohol | 2.0% |
| Ketotifen fumarate | 10.0% |
| Total Amount | 100% |

The above components except lauryl alcohol, sodium acetate and ketotifen fumarate were dissolved at 180° C. and mixed. Then the rest components were added and dispersed so as to have a homogeneous mixture. The mixture was laminated onto a PET film of 30 μm to have an adhesive layer of 100 μm, and a matrix type patch formulation of the present invention was prepared.

Example 20

| | |
|---|---|
| Sodium acetate | 0.5% |
| Liquid paraffin (Crystol 352) | 39.4% |
| Rosin tackifier (KR-610; manufactured by Arakawa Kagaku Co., Ltd.) | 32.5% |
| PIB (Vistanex MM-L-100) | 7.5% |
| SIS (Califlex D-1111) | 16.5% |
| BHT (Yoshinox) | 1.5% |
| Pirotiodecane | 2.0% |
| Ketotifen fumarate | 0.1% |
| Total Amount | 100% |

The above components except pirotiodecane, ketotifen fumarate and sodium acetate were dissolved at 180° C. and mixed. Then the rest components were added and dispersed so as to have a homogeneous mixture. The mixture was laminated onto a PET film of 30 μm to have an adhesive layer of 100 μm, and a matrix type patch formulation of the present invention was prepared.

Comparative Example 1

| | |
|---|---|
| SIS (Califlex D-1111) | 16.5% |
| PIB (Vistanex MM-L-100) | 1.5% |
| PIB (Vistanex LMMH) | 29.5% |
| Alicyclic saturated hydrocarbon resin (Arcon P-100) | |
| Liquid paraffin (Crystol 352) | 41% |
| Pirotiodecane | 2% |
| Ketotifen fumarate | 2% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Example 2

| | |
|---|---|
| SIS (Califlex D-1111) | 16.5% |
| PIB (Vistanex MM-L-100) | 1.5% |
| PIB (Vistanex LMMH) | 6% |
| Alicyclic saturated hydrocarbon resin (Arcon P-100) | 30% |
| Liquid paraffin (Crystol 352) | 38.5% |
| Pirotiodecane | 3% |
| Fentanyl citrate | 3% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Example 3

| | |
|---|---|
| SIS (Califlex D-1111) | 17.5% |
| PIB (Vistanex MM-L-100) | 2.5% |
| PIB (Vistanex LMMH) | 6% |
| Hardened rosin ester (Foral 85) | 35% |
| Liquid paraffin (Crystol 352) | 28% |
| Crotamiton | 5% |
| Pirotiodecane | 3% |
| Tizanidine hydrochloride | 1.5% |
| Aluminum silicate | 1% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Example 4

| | |
|---|---|
| SIS (Califlex D-1111) | 17.5% |
| PIB (Vistanex MM-L-100) | 2.5% |
| PIB (Vistanex LMMH) | 6% |
| Hardened rosin ester (KE-100) | 35% |
| Liquid paraffin (Crystol 352) | 20.5% |
| Glycol salicylate | 10% |
| 1-menthol | 5% |
| Tizanidine hydrochloride | 2% |
| Aluminum silicate | 1% |
| BHT (Yoshinox) | 0.5% |
| Total Amount | 100% |

All the components were hot-melted and applied onto a releasable liner paper to have a thickness of 100 m, and putted together with a backing so as to obtain a matrix type patch formulation.

Comparative Example 5

| | |
|---|---|
| PIB (Vistanex MM-L-100) | 38.4% |
| Hardened rosin ester (KE-311) | 20% |
| Liquid paraffin (Crystol 352) | 35.5% |
| Polybutene (HV-300) | 5% |
| 1-menthol | 0.1% |
| Tulobuterol hydrochloride | 1% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation.

Comparative Example 6

| | |
|---|---|
| SIS (Califlex D-1111) | 20% |
| Hardened rosin ester (KE-311) | 50% |
| Liquid paraffin (Crystol 352) | 25% |
| Lauryl alcohol | 1% |
| Alprenolol hydrochloride | 3% |
| BHT (Yoshinox) | 1% |
| Total Amount | 100% |

All the components were hot-melted and applied onto a releasable liner paper to have a thickness of 100 μm, and putted together with a backing so as to obtain a matrix type patch formulation.

Comparative Example 7

| | |
|---|---|
| SIS (Califlex D-1111) | 36.5% |
| PIB (Vistanex MM-L-100) | 3.5% |
| PIB (Vistanex LMMH) | 20% |
| Alicyclic saturated hydrocarbon resin (Arcon P-100) | 10% |
| Liquid paraffin (Crystol 352) | 25% |
| Sodium propionate | 0.2% |
| Ketotifen fumarate | 3.5% |
| Aluminum silicate | 0.8% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Example 8

| | |
|---|---|
| PIB (Vistanex MM-L-100) | 15% |
| Hardened rosin ester (Foral 85) | 70% |
| Crotamiton | 12.5% |
| Sodium acetate | 0.5% |
| Tizanidine hydrochloride | 2% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation.

Comparative Example 9

| | |
|---|---|
| SIS (Califlex D-1111) | 10% |
| PIB (Vistanex MM-L-100) | 5% |
| Alicyclic saturated hydrocarbon resin (Arcon P-100) | 20% |
| Liquid paraffin (Crystol 352) | 38% |
| Crotamiton | 5% |
| Sodium salicylate | 15% |
| Fentanyl citrate | 5% |
| Aluminum silicate | 1% |
| BHT (Yoshinox) | 1% |
| Total Amount | 100% |

All the components were hot-melted and applied onto a releasable liner paper to have a thickness of 100 μm, and putted together with a backing so as to obtain a matrix type patch formulation.

Comparative Example 10

| | |
|---|---|
| PIB (Vistanex MM-L-100) | 15% |
| Hardened rosin ester (Foral 85) | 10% |
| Liquid paraffin (Crystol 352) | 62% |
| Sodium acetate | 10% |
| Tulobuterol hydrochloride | 3% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation.

Comparative Example 11

| | |
|---|---|
| SIS (Califlex D-1111) | 26.5% |
| PIB (Vistanex MM-L-100) | 3.5% |
| PIB (Vistanex LMMH) | 20% |
| Hardened rosin ester (Foral 85) | 20% |
| Liquid paraffin (Crystol 352) | 25% |
| Sodium propionate | 0.2% |
| Alprenolol hydrochloride | 3.5% |
| Aluminum silicate | 0.8% |
| BHT (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Example 12

| | |
|---|---|
| PIB (Vistanex MM-L-100) | 16% |
| Hardened rosin ester (Foral 85) | 60% |
| Crotamiton | 20% |
| Sodium acetate | 1% |
| Tizanidine hydrochloride | 3% |
| Total Amount | 100% |

All the components were dissolved in toluene solvent, and applied onto a releasable liner paper to have a thickness of 100 μm. Then, the solvent was removed by drying and it was putted together with a backing so as to obtain a matrix type patch formulation.

Comparative Example 13

| | |
|---|---|
| SIS(Califlex D-1111) | 13.5% |
| PIB(Vistanex MM-L-100) | 4% |
| Hardened rosin ester(Foral 85) | 20% |
| Liquid paraffin(Crystol 352) | 25% |
| Liquid polybutene(HV-300) | 25% |
| Crotamiton | 5% |
| Sodium propionate | 1.2% |
| Tulobuterol hydrochlorlde | 5% |
| Aluminum silicate | 0.8% |
| BGH (Yoshinox) | 0.5% |
| Total Amount | 100% |

All the components were hot-melted and applied onto a releasable liner paper to have a thickness of 100 μm, and putted together with a backing so as to obtain a matrix type patch formulation.

Comparative Examples 1 to 6 are each corresponding to Examples 1 to 6, respectively. In each of Comparative Examples 1 to 6, a matrix type patch formulation was prepared in the same manner as described in the corresponding Example except that the organic acid or a salt thereof used in Examples 1 to 6 was not used, and that the amount of the plasticizer was increased.

In addition, Comparative Examples 7 to 13 are each corresponding to Examples 7 to 13, respectively. In each of Comparative Examples 7 to 13, a matrix type patch formulation was prepared in the same manner as described in the corresponding Example except that the absorption enhancer was not used and that the amount of the plasticizer was increased.

The transdermal permeable properties of each of the patch formulations obtained in Examples 1 to 13 and Comparative Examples 1 to 13, were evaluated by in vitro transdermal permeation test using human skin. Further, as to the skin irritations of each of the patch formulations obtained in Examples 1 to 6 and Comparative Examples 1 to 6, the skin irritant index (SI value) was determined using human skins.

Test Example 1

(Transdermal Permeation Test Using Human Skin)

After commercially obtaining freezed human abdominal skin, it was thawed and fats tissues in dermal side were removed carefully. Then the skin was adjusted to have a thickness of 350 μm using a dermatome, and installed in a flow-through cell (1 cm$^2$), in which hot water at 37° C. was circulated around the outer periphery, so that the dermal side is to be a receptor layer. Each of the matrix type patch formulations obtained in Examples 1 to 20 and Comparative Examples 1 to 6 was applied onto the stratum corneum side, and samplings were carried out at every one hour for 24 hours at a rate of 5 ml/hour using physiological saline to the receptor layer. The flow rates of the receiver solutions obtained at every one hour were determined accurately, and the drug concentrations were determined by a high-performance liquid chromatography method. The permeation rates per one hour were calculated, and the transdermal permeation rates in steady state were determined according to the following formula.

Transdermal Permeation Rate ($\mu g/cm^2/hr$)
= {Concentration of a Sample ($\mu g/ml$) × Flow Rate (ml)}
/ Applied surface area of the formulation ($cm^2$)

The results are shown in Table 1.

TABLE 1

| Example | Transdermal Permeation Rate ($\mu g/cm^2/hr$) |
| --- | --- |
| Example 1 | 1.35 |
| Comparative Example 1 | 0.03 |
| Example 2 | 1.45 |
| Comparative Example 2 | 0.15 |
| Example 3 | 1.78 |
| Comparative Example 3 | 0.08 |
| Example 4 | 2.23 |
| Comparative Example 4 | 0.12 |
| Example 5 | 1.03 |
| Comparative Example 5 | 0.05 |
| Example 6 | 1.87 |
| Comparative Example 6 | 0.15 |
| Example 7 | 2.05 |
| Comparative Example 7 | 0.13 |
| Example 8 | 1.24 |
| Comparative Example 8 | 0.19 |
| Example 9 | 3.67 |
| Comparative Example 9 | 0.25 |
| Example 10 | 2.45 |
| Comparative Example 10 | 0.17 |
| Example 11 | 3.76 |
| Comparative Example 11 | 0.10 |
| Example 12 | 2.89 |
| Comparative Example 12 | 0.32 |
| Example 13 | 3.08 |
| Comparative Example 13 | 0.57 |

Test Example 2
(Primary Irritant to Skin Test)

Each of the patch formulations obtained in Examples 1 to 6 and Comparative Examples 1 to 6 was stamped out into 10 $cm^2$, and applied onto a normal human skin in the back region for 24 hours. Right after releasing and at 24 hours after releasing, the skin conditions were observed by naked eyes, and the skin irritant index were determined in accordance with the criterion shown in Table 2. The results are shown in Table 3.

TABLE 2

| Result | Criterion Skin condition | Score |
| --- | --- | --- |
| − | No Reaction | 0 |
| ± | Slight Erythema(Rubor) | 0.5 |
| + | Erythema | 1.0 |
| ++ | Erythema & Edema | 2.0 |
| +++ | Erythema, Edema, Papule & Vesicle | 3.0 |
| ++++ | Bulla | 4.0 |

TABLE 3

| Example | Skin Irritant Index (SI value) |
| --- | --- |
| Example 1 | 3.0 |
| Comparative Example 1 | 5.6 |
| Example 2 | 8.5 |
| Comparative Example 2 | 11.3 |
| Example 3 | 5.7 |
| Comparative Example 3 | 10.2 |

TABLE 3-continued

| Example | Skin Irritant Index (SI value) |
| --- | --- |
| Example 4 | 13.7 |
| Comparative Example 4 | 16.4 |
| Example 5 | 5.8 |
| Comparative Example 5 | 8.5 |
| Example 6 | 18.3 |
| Comparative Example 6 | 19.6 |

Irritant Index = (Sum of the larger values of either right after the releasing or at 24 hours after the releasing of each subjects / number of subjects) × 100

Industrial Applicability

With the matrix type patch formulation of the present invention, the physiological active substance contained in the adhesive layer is absorbed via skins continuously into circulating blood in a high efficiency. In addition, the matrix type patch formulation of the present invention is extremely reduced in irritation to skin where the formulation is administered.

Further, with the matrix type patch formulation of the present invention, a continuous effective blood concentration of a drug can be attained, without being metabolized by the first-pass effect in liver which is shown with oral administration. Further, the side-effect which may be occurred owing to the rapid increases in blood concentration with oral administration, can be inhibited.

We claim:

1. A matrix patch formulation which comprises an adhesive layer containing an organic acid, a physiological active substance comprising a basic drug which forms an ion pair with said organic acid, a hydrophobic high molecular weight material, a tackifying resin, a plasticizer and an absorption enhancer, wherein said organic acid is an aliphatic carboxylic acid, an aromatic carboxylic acid, an alkyl sulfonic acid, an alkyl sulfonic acid derivative, a cholic acid derivative or a water-soluble inorganic salt thereof.

2. A matrix type patch formulation of claim 1, wherein the organic acid is an aliphatic carboxylic acid, an aromatic carboxylic acid, an alkyl sulfonic acid, an alkyl sulfonic acid derivative, a cholic acid derivative or a water-soluble inorganic salt thereof.

3. The matrix type patch formulation of claim 1 or 2, wherein the organic acid is N-2-hydroxyethyl piperidine-N'-2-ethane sulfonic acid, dehydrocholic acid or a water-soluble inorganic salt thereof.

4. The matrix type patch formulation of claim 2, wherein the water-soluble inorganic salt is sodium acetate, sodium propionate or sodium salicylate.

5. The matrix patch formulation according to claim 1, wherein the hydrophobic high molecular weight material is styrene-isoprene-styrene block copolymer, polyisobutylene or a blend of-the two materials.

6. The matrix patch formulation according to claim 1, wherein the tackifying resin is an alicyclic saturated hydrocarbon or a glycol ester of hardened resin.

7. The matrix patch formulation according to claim 1, wherein the placticizer is at least one selected from the group comprising paraffin, crotamiton, glycol salicylate and liquid polybutene.

8. The matrix patch formulation according to claim 1, wherein the adsorption enhancer is 1-menthol, lauryl alcohol or pirotiodecane.

9. The matrix patch formulation of claim 1, wherein the adhesive layer contains 0.1 to 20% (w/w) of the physiological active substance, 0.01 to 15% (w/w) of the organic acid, 15 to 60% (w/w) of the hydrophobic high molecular weight material, 10 to 70% (w/w) of the tackifying resin, 10 to 60% (w/w) of the plasticizer and 0.01 to 20% (w/w) of the absorption enhancer.

10. The matrix patch formulation of claim 1, wherein the adhesive layer contains 0.1 to 20% (w/w) of the physiological active substance, 0.1 to 10% (w/w) of the organic acid, 15 to 50% (w/w) of the hydrophobic high molecular weight material, 10 to 60% (w/w) of the tackifying resin, 15 to 50% (w/w) of the plasticizer and 0.1 to 10% (w/w) of the absorption enhancer.

11. The matrix patch formulation of claim 1, wherein the adhesive layer contains 0.1 to 20% (w/w) of the physiological active substance, 0.1 to 5% (w/w) of the organic acid, 20 to 40% (w/w) of the hydrophobic high molecular weight material, 20 to 50% (w/w) of the tackifying resin, 20 to 40% (w/w) of the plasticizer and 0.1 to 5% (w/w) of the absorption enhancer.

12. The matrix patch formulation according to claim 1, wherein the basic drug is a bronchodilator.

13. The matrix patch formulation according to claim 1, wherein the basic drug is an antiarrhythmic agent.

14. The matrix patch formulation according to claim 1, wherein the basic drug is a narcotic analgesic agent.

15. The matrix patch formulation according to claim 1, wherein the basic drug is a cardiovascular agent.

16. The matrix patch formulation according to claim 1, wherein the basic drug is a skeletal muscle relaxant.

17. The matrix patch formulation according to claim 1, wherein the basic drug is an antiallergic agent.

* * * * *